United States Patent [19]

Bey et al.

[11] Patent Number: 5,614,557
[45] Date of Patent: Mar. 25, 1997

[54] METHOD OF CONTROLLING TUMOR GROWTH RATE

[75] Inventors: Philippe Bey, Strasbourg; Michel Jung, Graffenstaden, both of France

[73] Assignee: Marion Merrell et Compagnie C/O Merrell Pharmaceuticals Inc., Cincinnati, Ohio

[21] Appl. No.: 403,531

[22] Filed: Mar. 14, 1995

Related U.S. Application Data

[63] Continuation of Ser. No. 284,706, Aug. 2, 1994, abandoned, which is a continuation of Ser. No. 137,397, Oct. 14, 1993, abandoned, which is a continuation of Ser. No. 2,521, Jan. 11, 1993, abandoned, which is a continuation of Ser. No. 874,989, Apr. 24, 1992, abandoned, which is a continuation of Ser. No. 759,633, Sep. 12, 1991, abandoned, which is a continuation of Ser. No. 534,008, Jun. 1, 1990, abandoned, which is a continuation of Ser. No. 431,685, Nov. 3, 1989, abandoned, which is a continuation of Ser. No. 334,733, Apr. 6, 1989, abandoned, which is a continuation of Ser. No. 228,789, Aug. 4, 1988, abandoned, which is a continuation of Ser. No. 110,639, Oct. 15, 1987, abandoned, which is a continuation of Ser. No. 639,977, Aug. 10, 1984, abandoned, which is a division of Ser. No. 382,265, May 26, 1982, abandoned, which is a continuation of Ser. No. 262,834, May 12, 1981, abandoned, which is a continuation-in-part of Ser. No. 204,749, Nov. 7, 1980, abandoned, which is a continuation of Ser. No. 28,757, Apr. 10, 1979, abandoned, which is a continuation-in-part of Ser. No. 814,765, Jul. 11, 1977, abandoned.

[51] Int. Cl.$^6$ .......................... A01N 37/44; A61K 31/195
[52] U.S. Cl. .............................. 514/561; 514/34; 514/632
[58] Field of Search ........................ 514/561, 632

[56] References Cited

U.S. PATENT DOCUMENTS

| | | | |
|---|---|---|---|
| 2,662,915 | 12/1953 | Lontz et al. | 260/534 |
| 3,168,558 | 2/1965 | Kurhajec et al. | 260/534 R |
| 4,207,315 | 6/1980 | Voorhees et al. | 424/319 |
| 4,288,601 | 9/1981 | Kollonitsch | 562/561 |
| 4,325,961 | 4/1982 | Kollonitsch | 562/561 |
| 4,418,077 | 11/1983 | Bey | 562/561 |
| 4,423,073 | 12/1983 | Gerhart | 562/561 |
| 4,439,619 | 3/1984 | Bey | 562/561 |
| 4,446,151 | 5/1984 | Gerhart | 562/561 |

FOREIGN PATENT DOCUMENTS 559737  7/1958  Canada ............................ 260/534 G

OTHER PUBLICATIONS

H-A. Williams et al., De Italian J. Biochem. 25, pp. 5–32 (1976).
Raiwa et al., Medical Biology 53, pp. 121–147 (1975).
Russell, Life Sciences, 13, pp. 1635–1647 (1973).
Janfe et al., Biochem and Biophys. Res Comm. 42, pp. 222–229 (1971).
Pegg et al, Biochem, J. 108, pp. 533–539 (1968).
Organic Synthesis, III, pp. 440–442 (1955).
Synthesis pp. 791–793 (1973).
Hackh's "Chemical Dictionary" 4th Ed. Copyright renewed 1972. McGraw-Hill Publ. p. 36.
Pauling, Linus "The Nature of the Chemical Bond" 2nd Ed. Cornell University Press. (1948) p. 60.
Relyea, Noel et al. "Potent inhibition of ornithine decarboxylase by *beta–gamma*–unsaturated substrate analogs." Biochem. Biophysics Res. Commun. 1975 67(1) 392–402.
Rando, Robert R. "Chemistry and Enzymology of $k_{cat}$ Inhibitors." Science, vol. 185 pp. 320–324. (Jul. 26, 1974).
Viterro et al, Tetrahedron letters pp. 4617–4620 (1971).
Dunzendorfer et al., Cancer Research 38, pp. 2321–2324 (1978).
Rando, "Chemistry, Enzymology of $K_{C3}T$ Inhibitors" Science, vol. 185, pp. 320–324 (Jul. 26, 1974).
J. of Medicinal Chemistry, vol. 17, No. 4, pp. 447–451 (1974) and vol. 18, No. 6, pp. 600–604 (1975).
Burger, Medicinal Chemistry, 3rd Ed., Part I, Pub. Wiley Interscience, N.Y., pp. 65, 70–72 (1970).
Clinical Aspects of Inhibition of Ornithine Decarboxylase With Emphasis on Therapeutic Trials of Eflornithine (DFMO) in Cancer and Protozoan Diseases – Chapter 16 of *Inhibition of Polyamine Metabolism*, P. McCann, A. Pegg and A. Sjoerdsma (1987).

*Primary Examiner*—Jerome D. Goldberg
*Attorney, Agent, or Firm*—Louis J. Wille

[57] ABSTRACT

α-Fluoromethyl- or α-difluoromethylornithine, and certain derivatives thereof, can be used alone or in combination with cytotoxic agents for the treatment of neoplastic diseases.

3 Claims, No Drawings

METHOD OF CONTROLLING TUMOR GROWTH RATE

This is a continuation of application Ser. No. 08/284,706, filed Aug. 2, 1994; now abandoned which is a continuation of application Ser. No. 08/137,397, filed Oct. 14, 1993, now abandoned; which is a continuation of application Ser. No. 08/002,521, filed Jan. 11, 1993, now abandoned; which is a continuation of application Ser. No 07/874,989, filed Apr. 24, 1992, now abandoned; which is a continuation of application Ser. No. 07/759,633, filed Sep. 12, 1991, now abandoned; which is a continuation of application Ser. No. 07/534,008, filed Jun. 1, 1990, now abandoned; which is a continuation of application Ser. No. 07/431,685, filed Nov. 3, 1989, now abandoned; which is a continuation of application Ser. No 07/334,733, filed Apr. 6, 1989, now abandoned; which is a continuation of application Ser. No. 07/228,789, filed Aug. 4, 1988, now abandoned; which is a continuation of application Ser. No. 07/110,639, filed Oct. 15, 1987, now abandoned; which is a continuation of application Ser. No 06/639,977, filed Aug. 10, 1984, now abandoned; which is a divisional of application Ser. No. 06/382,265, filed May 26, 1982, now abandoned; which is a continuation of application Ser. No. 06/262,834, filed May 12, 1981, now abandoned; which is a continuation-in-part of application Ser. No. 66/204,749, filed Nov. 7, 1980, now abandoned; which is a continuation of application Ser. No. 06/028,757, filed Apr. 10, 1979; now abandoned, which is a continuation-in-part of application Ser. No. 05/814,765, filed Jul. 11, 1977, now abandoned, which is herein incorporated by reference.

This invention relates to the use of certain α-fluoromethyl ornithine derivatives for controlling tumor growth rate.

The invention sought to be patented comprehends a method of controlling the growth rate of rapidly proliferating tumor tissue in a patient in need thereof, which comprises administering to said patient an effective amount of a compound of the formula:

$$R_aHN(CH_2)_3-\underset{NHR_b}{\underset{|}{C}}-\overset{Y}{\underset{}{\overset{|}{C}}}-\overset{O}{\underset{}{\overset{\|}{C}}}-R_1$$

wherein:
Y is $FCH_2-$, $F_2CH-$, or $F_3C-$;
$R_a$ and $R_b$ are, independently, hydrogen, $(C_1-C_4)$alkylcarbonyl, or the group

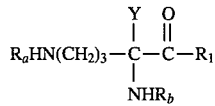

wherein $R_2$ is hydrogen, $(C_1-C_4)$alkyl, benzyl, or p-hydroxybenzyl;
$R_1$ is hydroxy, $(C_1-C_8)$alkoxy, the group $-NR_4R_5$, wherein $R_4$ and $R_5$ are, independently, hydrogen, or $(C_1-C_4)$ alkyl, or the group

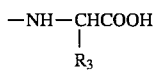

wherein $R_3$ is hydrogen, $(C_1-C_4)$alkyl, or p-hydroxybenzyl; and the pharmaceutically acceptable salts and individual optical isomers thereof.

As used in Formula I, the term "$(C_1-C_4)$alkylcarbonyl" means the group —CO-alkyl wherein the alkyl moiety has from 1 to 4 carbon atoms and is straight or branched, for example, methyl, ethyl, n-propyl, isopropyl, n-butyl, and isobutyl and tert-butyl. The term "$(C_1-C_4)$alkyl" means a straight or branched alkyl group having from 1 to 4 carbon atoms, such as methyl, ethyl, n-propyl, n-butyl, isopropyl and tert-butyl. The term "$(C_1-C_8)$alkoxy" means an alkoxy group containing a straight or branched alkyl moiety having from 1 to 8 carbon atoms. Examples of $(C_1-C_8)$alkoxy groups are methoxy, ethoxy, n-butoxy, n-pentyloxy, i-propoxy, and n-pentyloxy. Illustrative acid addition salts of the compounds of the Formula I are the salts obtained with non-toxic inorganic acids, such as hydrochloric, hydrobromic, sulfuric, and phosphoric acids, as well as organic acids, such as cyclamic, acetic, glycolic, lactic, pyruvic, malonic, succinic, glutaric, fumaric, malic, tartaric, citric, ascorbic maleic, hydroxymaleic, benzoic, p-hydroxybenzoic, phenylacetic, cinnamic, salicylic, 2-phenoxybenzoic, and sulfonic acids, such as methane sulfonic acid.

Also included are non-toxic salts formed with any suitable inorganic or organic base. Illustratively, these salts include those of the alkali metals, as for example, sodium, potassium and lithium; alkaline earth metals, such as calcium and magnesium; light metals of Group IIIA including aluminium; and organic primary, secondary, and tertiary amines, as for example, trialkylamines, including cyclohexylamine, ethylamine, pyridine, methylaminomethanol, ethanolamine, piperazine and other amines which are known by those skilled in the art to form non-toxic salts. The salts are prepared by conventional means.

Preferred embodiments of the compounds of Formula I are those wherein $R_1$ is hydroxy. More preferred embodiments are the compounds of Formula I wherein $R_1$ is hydroxy and Y is $FCH_2-$ or $F_2CH-$. Still more preferred embodiments are the compounds of Formula I wherein either $R_a$ or $R_b$ is hydrogen, $R_1$ is hydroxy, and Y is $-CH_2F$ or $-CHF_2$.

Preferred compounds of Formula I are 2,5-diamino-2-difluoromethylpentanoic acid ("α-difluoromethylornithine" or "α-DFMO") and 2,5-diamino-2-fluoromethylpentanoic acid ("α-monofluoromethylornithine" or "α-MFMO").

It should be noted that the compounds of Formula I have an asymmetric center at the carbon atom which is alpha to the carboxyl group. Accordingly, the compounds may exist in either of their D- or L-configurations or as their DL-racemates. As used herein, the compounds are intented to be used as their racemic mixtures or as individual active enantiomers.

The compounds of Formula I produce in vivo irreversible inhibition of ornithine decarboxylase (ODC), the enzyme which catalyzes the decarboxylation of ornithine to putrescine. The decarboxylation of ornithine to putrescine is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-adenosyl S-methyl homocysteamine is formed by the decarboxylation of S-adenosylmethionine (SAM), a reaction catalyzed by the enzyme S-adenosylmethionine decarboxylase (SAM-DC). Since putrescine is a precursor of the polyamines, it is seen that blockade of the conversion of ornithine to putrescine, such as by inhibition of ODC, can provide a method for regulating the cellular levels of the polyamines.

The polyamines, which are found in animal tissues and microorganisms, are known to play an important role in cell growth and proliferation. The induction of cell growth and proliferation is associated with a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus; in psoriatic skin lesions; and in other cells undergoing rapid growth processes.

It is well known that the rapid proliferation of tumor tissue is marked by an abnormal elevation of polyamine levels. Hence, the polyamines may play an important role in the maintenance of tumor growth. It is believed that the compounds of Formula I may exert their therapeutic effect by blocking the formation of the polyamines and thereby slowing interrupting, or arresting the proliferation of the tumor tissue. It should be understood, however, that the process of this invention is not meant to be limited by any particular theory or mode of action.

The ability of the compounds of Formula I to irreversibly inhibit ornithine decarboxylase in vivo can be demonstrated as follows: An aqueous solution of the appropriate compound is given orally or parenterally to male mice or rats. The animals are sacrificed 1 to 48 hours after administration of the compound, and the ventral lobes of the prostate removed and homogenized. The activity of ornithine decarboxylase is measured as generally described by E. A. Pegg and H. G. Williams-Ashman, Biochem. J. 108, 533–539 (1968).

As used herein, the term "tumor tissue" means both benign and malignant tumors or neoplasms, and includes melanomas, lymphomas, leukemias, and sarcomas. Illustrative examples of tumor tissues are cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseus or non-osseus sarcomas, breast tumors; tumors of the pituitary, thyroid and adrenal cortex; gastrointestinal tumors, such as those of the esophagus, stomach, intestine and colon; pancreatic and hepatic tumors; and lung tumors. The term "controlling the growth", as used herein, means slowing, interrupting, arresting, or stopping the growth of a rapidly proliferating tumor in a warm blooded animal. It should be understood that the administration of a compound of Formula I to a warm blooded animal in the absence of a cytotoxic agent does not provide a "cure" for the tumor in the sense that the tumor tissue is destroyed or totally eliminated from the body of the animal being treated.

For the purposes of this invention, a compound of Formula I can be administered to the patient in conjunction with other therapeutic methods or in combination with chemical agents known in the art to be useful for tumor therapy. For example, a compound of Formula I can be administered in conjunction with surgical excision of the tumor or with radiation therapy, immunotherapy, or local heat therapy. Moreover, in a preferred manner, a compound of Formula I can be adminstered to a patient in combination with a chemical cytotoxic agent known in the art to be useful for tumor therapy. When such combination therapy is employed for the treatment of a tumor, the cytotoxic agent may be administered at a dosage known in the art to be effective for treating the tumor. However, a compound of Formula I may produce an additive or synergistic effect with a cytotoxic agent against a particular tumor. Thus, when such combination antitumor therapy is used, the dosage of the cytotoxic agent administered may be less than that administered when the cytotoxic agent is used alone. In combination with a compound of Formula I, the cytotoxic agent may, therefore, be administered at a lower dosage level or at less frequent intervals as compared to the cytotoxic agent when used alone.

In combination with a compound of Formula I, any cytotoxic agent may be employed. Illustrative examples of cytotoxic agents are: cyclophosphamide, methotrexate, prednisone 6-mercaptopurine, procarbazine, daunorubicin, vincristine, vinblastine, chlorambucil, cytosine arabinoside, 6-thioguanine, thio TEPA, 5-fluorouracil, 5-fluoro-2-deoxyuridine, 5-azacytidine, nitrogen mustard, 1,3-bis (2-chloroethyl)-1-nitrosourea (BCNU), (1-(2-chloroethyl)-3-cyclohexyl-1-nitrosourea) (CCNU), busulfan, adriamycin, bleomycin, vindesine, cycloleucine, or MGBG. Other cytotoxic agents will be apparent to those skilled in the art.

The effect of the compounds of Formula I for the control of the growth rate of rapidly proliferating tumor tissue can be assessed in standard animal tumor models. For example, the anti-tumor effect of $\alpha$-difluoromethylornithine (DFMO) has been demonstrated in the following animal tumor models: (a) L1210 leukemia in mice, (b) EMT6 tumor in Balb/C mice, (c) 7,12-dimethylbenzanthracene-induced (DMBA-induced) mammary tumor in rats, and (d) Morris 7288C or 5123 hepatoma in Buffalo rats. In addition, the anti-tumor effect of DFMO in combination with various cytotoxic agents has been demonstrated as follows: (a) in combination with vindesine or adriamycin in L1210 leukemia in mice, in Morris 7288C hepatoma in Buffalo rats, and in EMT6 tumor in mice, (b) in combination with cytosine arabinoside in L1210 leukemia in mice, (c) in combination with methotrexate in L1210 leukemia in mice, (d) in combination with cyclophosphamide in EMT6 tumor in mice and in DMBA-induced tumor in mice, (e) in combination with BCNU in mouse glioma 26 brain tumor, and (f) in combination with MGBG in L1210 leukemia in mice, in Morris 7288C hepatoma in Buffalo rats, in P388 lymphocytic leukemia in mice, and in S-180 sarcoma in rats.

The method of the present invention is particularly advantageous in that the compounds employed are essentially non-toxic.

When, in the treatment of a malignant neoplastic disease, a compound of Formula I is administered in combination with a cytotoxic agent, the therapeutic effect of the cytotoxic agent may be potentiated. The remission produced by the cytotoxic agent may be enhanced and regrowth of the tumor tissue may be slowed or prevented. Use of such combination therapy therefor allows smaller doses or fewer individual doses of the cytotoxic agent to be employed. Thus, the detrimental and/or debilitating side effects of the cytotoxic agent are minimized while, at the same time, the anti-tumor effects are enhanced. The term "combination therapy" contemplates the administration of a compound of Formula I immediately prior to the beginning of therapy with a cytotoxic agent, concomitantly with such therapy, or during the period of time immediately following cessation of such therapy. Preferably, the patient is treated with a compound of Formula I for about 1 to 14 days, preferably 4 to 14 days, prior to the beginning of therapy with a cytotoxic agent, and thereafter, on a daily basis during the course of such therapy. Daily treatment with the compound of Formula I can be continued for a period of , for example, 1 to 365 days after the last dose of the cytotoxic agent is administered.

When such combination therapy results in remission of the tumor, and all tumor cells are not destroyed, regrowth of the tumor may be prevented or slowed indefinitely by continued treatment with a compound of Formula I. Thus, a compound of Formula I can be administered to stop or slow the growth of the tumor during the periods when therapy using a cytotoxic agent may be temporarly discontinued.

A preferred cytotoxic agent for combination therapy with a compound of Formula I is methylglyoxal bis(guanylhydrazone), herein referred to as MGBG. The preferred compounds of Formula I for use in combination therapy with MGBG are those wherein Y is $CHF_2$ or $CH_2F$, the most preferred compound of Formula I being 2,5-diamino-2-difluoromethylpentanoic acid (α-DFMO) or an optical isomer or a pharmaceutically acceptable salt thereof. MGBG is an inhibitor of S-adenosyl methionine decarboxylase. The activity of MGBG as a cytotoxic agent in the treatment of neoplastic diseases is well documented. For example, W. A. Knight et al., Cancer Treat Rep., 43, 1933, (1979) have reported that a dose of MGBG administered intravenously once or twice week to patients in the advanced stages of carcinoma of the bladder, esophagus, lung, pancreas, colon, kidney, breast and prostate, oat cell carcinoma, adenocarcinoma, lymphoma, hepatoma, melanoma, leukemia, or Ewing's sarcoma produced measurable regression of the tumor in many of the patients treated and complete disappearance of the disease in two of the 65 treated patients.

The amount of MGBG to be administered may be the same as the amount known in the art to be effective for tumor therapy. Effective and non-toxic dosages are determined by the physician in each case, taking into account the condition of the individual patient. For example, a dosage of 250–500 mg. per meter$^2$ of body surface area may be infused once or twice weekly in 100 ml. of aqueous 5% dextrose solution over a 30 minute period. Combination therapy with a compound of Formula I improves the response of the tumor tissue to the cytotoxic effect of MGBG and permits the use of a smaller individual dose of MGBG and a shorter course of treatment than would be required with the use of MGBG alone.

Suitable dosages of 2,5-diamino-2-difluoromethylpentanoic acid or of other compounds of Formula I for use in combination therapy with MGBG or other cytotoxic agents can be any amount effective in inhibiting polyamine biosynthesis sufficiently to control the tumor growth rate or to achieve a heightened response to the cytotoxic agent administered in conjunction therewith.

The synergistic cytotoxic effect on tumor tissue of a compound of Formula I in combination with MGBG can be demonstrated quantitatively in cultures of HeLa cells. A HeLa cell culture grown under standard laboratory conditions was treated with MGBG at a concentration of 7 μM alone and with the same dosage of MGBG after pretreatment with 2,5-diamino-2-difluoromethylpentanoic acid (2.5 mM) for 4 days. The cell culture treated with MGBG alone showed a 25% cell kill, whereas the culture pretreated with a compound of the present invention showed a cell kill of 97%.

As pharmacologically useful agents, the compounds of Formula I can be administered in various manners to the patient being treated to achieve the desired effect. The compounds can be administered either alone or in combination with one another, or they can be administered in the form of pharmaceutical compositions, which are well known in the art. The compounds may be administered orally or parenterally (for example, intravenously, intraperitoneally, or subcutaneously), including injection of the active ingredient directly into the tumor. The amount of compound administered will vary over a wide range and can be any effective amount. Depending upon the patient to be treated, the severity of the condition being treated, the mode of administration, and the particular compound employed, the effective amount of compound administered will vary from about 1 mg/kg to 2000 mg/kg of body weight of the patient per day and preferably will be about 10 mg/kg to 500 mg/kg of body weight of patient per day. For example, a typical unit dosage form may be a tablet containing from 100 to 500 mg of a compound of Formula I which may be administered to the patient being treated 1 to 10 times daily to achieve the desired effect.

As used herein the term patient is taken to mean warm blooded animals such as mammals, for example dogs, rats, mice, cats, guinea pigs, horses, bovine cows, sheep, and humans.

The solid unit dosage forms can be of the conventional type. Thus, the solid form can be a capsule which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of Formula I wherein $R_1$ is hydroxy and each of $R_a$ and $R_b$ is hydrogen are prepared by treating an ester derivative of ornithine, wherein the amino groups are suitably protected, with a strong base to form the carbanion intermediate which is reacted With a suitable halomethylhalo alkylating reagent in an aprotic solvent, such as, dimethylsulfoxide, dimethylformamide, dimethylacetamide, benzene, toluene, ethers, such as, tetrahydrofuran, diethyl ether or dioxane and in the presence of hexamethylphosphortriamide, when Y is other than $F_2CH-$, at a temperature of about −120° C. to 120° C., preferably about 25° to 50° C. for about ½ hour to 48 hours followed by acid or base hydrolysis as represented by the following reaction sequence.

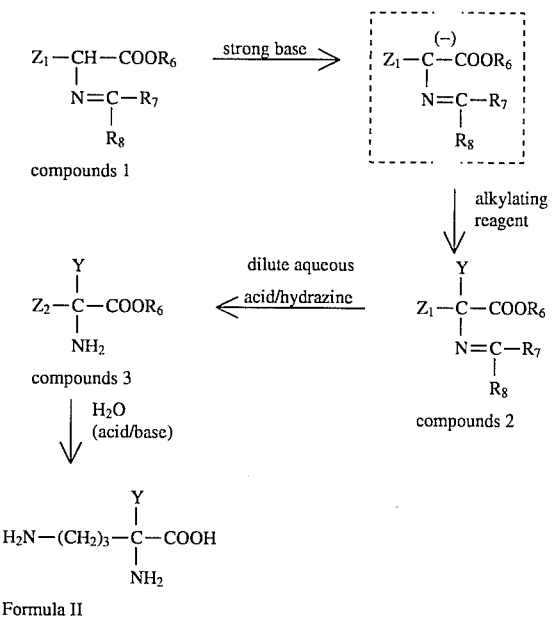

compounds 1 compounds 2 compounds 3

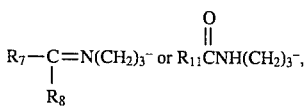

Formula II

In the above reaction sequence Y is $FCH_2-$, $F_2CH-$, or $F_3C-$; $R_6$ is $(C_1-C_4)$ alkyl (for example, methyl, ethyl, isopropyl, n-propyl or n-butyl) ; $R_7$ is hydrogen, phenyl, alkyl, methoxy or ethoxy; $R_8$ is phenyl or $(C_1-C_8)$ alkyl; or $R_7$ and $R_8$ taken together may form an alkylene group of from 5 to 7 carbon atoms, that is, $-CH_2-(CH_2)_m-CH_2-$ wherein m is an integer of from 3 to 5; $Z_1$ is $$R_7-\underset{R_8}{\overset{O}{\underset{|}{C}}}=N(CH_2)_3^- \text{ or } R_{11}\overset{O}{\overset{\|}{C}}NH(CH_2)_3^-,$$

wherein $R_7$ and $R_8$ are the same and have the meanings defined above, and is phenyl, benzyl, or $C_1-C_4$ alkyl (for example, methyl ethyl or isopropyl) and $Z_2$ is $H_2N(CH_2)_3-$ or $$R_{11}\overset{O}{\overset{\|}{C}}NH-(CH_2)_3^-$$

wherein $R_{11}$ has the above defined meanings. Illustrative examples of straight or branched $(C_1-C_8)$ alkyl groups which $R_7$ and $R_8$ may represent, are, for example, methyl, ethyl, n-propyl, isopropyl, n-butyl, tert-butyl, n-pentyl, neopentyl or triethylmethyl.

Suitable strong bases which may be employed in the above reaction sequence to form the carbanion intermediate are those which will abstract a proton from the carbon atom alpha to the carboxy group, such as an alkyl lithium, for example, butyl lithium or phenyl lithium; lithium di-alkylamides, for example, lithium diisopropylamide; lithium amide; sodium or potassium t-butylate; sodium amide; metal hydrides, for example, sodium hydride or potassium hydride; tertiary amines, such as, triethylamine; lithium acetylide; or dilithium acetylide. Lithium acetylide, dilithium acetylide, sodium hydride, lithium diisopropylamide, and tertiary sodium butylate are particularly preferred bases.

Suitable alkylating reagents which may be employed in the above reaction sequence are illustratively chlorofluoromethane, bromofluoromethane, fluoroiodomethane, chlorodifluoromethane, bromodifluoromethane, difluoroiodomethane, bromotrifluoromethane, chlorotrifluoromethane, and trifluoroiodomethane. When chlorodifluoromethane, bromodifluoromethane, and difluoroiodomethane are used for the alkylative reaction, rapid addition of the halomethyl halo reagent to the carbanion intermediate derived from the compounds of Formula I is necessary for optimal yields. The alkylating reagents are known in the art.

Removal of the protecting groups of the amine and carboxylic function may be achieved in one step by treatment of compounds 2 with aqueous acid, for example, hydrochloric acid or toluene sulfonic acid at a temperature of about 0° to 160° C. for about 4 to 24 hours to give compounds of Formula II. It is preferred to remove first the protecting groups of the amine function(s) of compounds 2 when said functions are protected as a Schiff's base by treating compounds 2 with dilute aqueous acid, for example, hydrochloric acid on with hydrazine or phenylhydrazine in solvents, such as, lower alcohols, for example, methanol or ethanol, ethers, chlorinated hydrocarbons, benzene and water. Removal of the protecting groups of the carboxylic functions and the amine groups when the amine groups are protected other than as a Schiff's base is achieved by treatment of compounds 3 with concentrated aqueous acids, for example, hydrobromic acid at a temperature of about 0° to 160° C. or in aqueous bases, for example, ammonium hydroxide.

The amine protected ester derivatives, that is, compounds 1, wherein $R_7$ is other than methoxy or ethoxy, are prepared by treating an appropriate amino acid ester with a carbonyl bearing compound to form a Schiff's base in a generally known manner, specifically: (a) when $R_7$ is hydrogen, by treating the appropriate amino acid ester with benzaldehyde or an alkanal having from 1 to 9 carbon atoms being straight or branched, for example, 1-propanal, 1-butanal, 2,2-dimethylpropan-1-al or 2,2-diethylbutan-1-al; (b) when $R_7$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_7$ is a straight or branched alkyl group having from 1 to 8 carbon atoms, treating the appropriate amino acid ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When in compounds 1 $R_7$ is methoxy or ethoxy, an appropriate amino acid ester derivative is reacted with benzoyl halide, for example, chloride, or an alkanoic acid halide, for example, chloride, wherein the alkanoic acid has from 1 to 9 carbon atoms and may be straight or branched, such as, acetyl chloride, propionyl chloride, butyryl chloride, tert-butyryl chloride, 2,2-diethylbutyric acid chloride or valeryl chloride, at 0° C. in etherst methylenechloride, dimethylformamide, dimethylacetamide or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonlure hexafluorophosphate when $R_7$ is methoxy or triethyloxonium tetrafluoroborate when $R_7$ is ethoxy at about 25° C. in a chlorinated hydrocarbon solvent such as methylene chloride, chlorobenzene or chloroform, and the reaction mixture is refluxed for about 12 to 20 hours. The mixture is then cooled at about 25° C. and an organic base such as triethylamine or pyridine is added after which the solution is extracted with brine and the product isolated.

When in compounds 1 $R_7$ and $R_8$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

When in compounds 1, $Z_1$ is

the

protecting group is added to ornithine by treatment of said amino acid with an excess of copper salt, for example, copper carbonate in boiling water for about 1 to 6 hours, and upon cooling to room temperature the insoluble materials are filtered off, and the filtrate is treated with an appropriate acid halide, for example, in acetone in the presence of a base such as sodium bicarbonate or sodium hydroxide followed by treatment with hydrogen sulfide; Illustrative acid halides which may be employed are acetyl chloride, propionyl chloride, benzoyl chloride or 2-phenylacetyl chloride.

The amino acid ester is formed by generally known procedures, for example, the amino acid is treated with an appropriate alcohol, such as, methanol, ethanol, or n-butanol saturated with HCl gas.

The compounds of Formula I wherein $R_a$ and $R_b$ are hydrogen, $R_1$ is hydroxy, and Y is —CH$_2$F or —CHF$_2$ can be made by an alternative method, which is illustrated herein by Example 10 which describes the preparation of 2,5-diamino-2-fluoromethylpentanoic acid (α-monofluoromethyl ornithine or α-MFMO). α-DFMO can be prepared by an obvious modification of this process employing difluoroacetcnitrile in place of fluoroacetonitrile.

Following is described the preparation of compounds of Formula I wherein $R_a$ and/or $R_b$ are other than hydrogen. The following description is applicable to all the above said compounds, however, it is necessary to protect one or the other of the amino groups prior to treatment with the appropriate reactant, that is, acid halide or anhydride, alkyl haloformate or acid of the formula

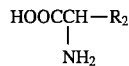

or anhydride thereof as described below to give compounds wherein either or both of $R_a$ and $R_b$ is other than hydrogen as follows: when $R_a$ is hydrogen and $R_b$ is other than hydrogen, the amino group to which $R_b$ is attached is protected as a copper salt by treatment of the corresponding derivative wherein $R_a$ and $R_b$ are hydrogen with an excess of a copper salt, for example, copper carbonate after which the amino group to which $R_a$ is attached is protected with, for example, benzyloxycarbonyl or tert-butoxycarbonyl by treatment with benzyl chloroformate or tert-butoxycarbonyl azide respectively followed by treatment with hydrogen sulfide, by procedures generally known in the art and illustrated more fully in the specific examples contained herein, prior to treatment with the appropriate reactant described below to give compounds wherein $R_b$ is other than hydrogen. The $R_a$ amine protecting group is subsequently removed by treatment with acid, for example, trifluoroacetic acid, HBr in dioxane or HBr in acetic acid or hydrogenolysis. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different. In preparing compounds wherein $R_a$ is other than hydrogen and $R_b$ is hydrogen the amino group to which $R_b$ is attached is protected as a copper salt by treatment of the corresponding derivative wherein each $R_a$ and $R_b$ is hydrogen with an excess of copper salt, for example, copper carbonate prior to treatment with the appropriate reactant described below followed by acid or base hydrolysis and subsequently treating with hydrogen sulfide.

The compounds of Formula I wherein $R_a$ or $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or as to compounds of Formula I, $R_a$ is other than hydrogen as described above and $R_1$ is hydroxy with an acid halide of the formula

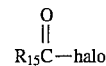

wherein halo is a halogen atom, for example, chlorine or bromine and $R_{15}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with acid or hydrogenolysis.

The compounds of Formula I wherein $R_a$ or $R_b$ is

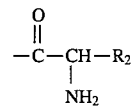

wherein $R_2$ is hydrogen, a straight or branched lower alkyl group of from 1 to 4 carbon atoms, benzyl or p-hydroxybenzyl and $R_1$ is hydroxy are prepared by treating the corresponding derivative wherein $R_a$ or $R_b$ is hydrogen or is suitably protected or as to compounds of Formula I, $R_b$ is other than hydrogen as described hereinabove with an acid of the formula

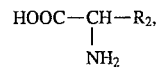

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate, hydrogenolysis to remove the protecting groups.

The compounds of the Formula I wherein $R_1$ is a straight or branched alkoxy group of from 1 to 8 carbon atoms are prepared by converting the corresponding compounds wherein $R_1$ is hydroxy to the acid halide by, for example, treatment with thionyl chloride, followed by alcoholysis with an alcohol of the formula $R_{17}OH$ wherein $R_{17}$ is a straight or branched alkyl group having from 1 to 8 carbon atoms by procedures generally known in the art. Alternatively, compounds of Formula I wherein $R_1$ is a straight or branched alkoxy group of from 1 to 8 carbon atoms may be prepared from the corresponding derivative wherein $R_1$ is hydroxy by treatment of said derivative with an alcohol of the formula $R_{17}OH$ as defined above saturated with HCl for about 30 minutes for 12 hours at a temperature of about 25° C. to the boiling point of the alcohol.

The compounds of this invention wherein $R_1$ is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein $R_1$ is hydroxy and $R_a$ and $R_b$ have the meanings defined in Formula I with the proviso that any free amino group is suitably protected with groups, such as, carbobenzyloxy or tert-butoxycarbonyl with an excess of an appropriate amine which may be represented as $HNR_4R_5$. The reaction is carried out in methylene chloride, chloroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamines; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of Formula I wherein $R_1$ is

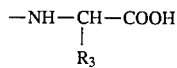

are prepared by reacting the corresponding derivative wherein in $R_1$ is hydroxy or a functional derivative thereof, such as, an acid anhydride and $R_a$ and $R_b$ have the meanings defined in Formula I with the proviso that any free amino group is protected with a suitable blocking group, such as, benzyloxycarbonyl, tert-butoxycarbonyl by reacting the amine protected free acid with a compound of the structure

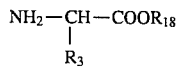

wherein $R_3$ has the meaning defined in Formula I and $R_{18}$ is a lower alkyl group, for example, methyl or ethyl in an ether solution, such as, tetrahydrofuran or dioxane at about 0° C. to 35° C. for abut 1 to 20 hours followed by acid then base hydrolysis, for example, with 2N aqueous $NH_3$ at about 0° to 50° C. for about 1 to 20 hours, to remove the protecting group(s), with the proviso that when the amine protected free acid is employed the reaction is carried out using a dehydrating agent such as dicyclohexylcarbodiimide.

The lactams of the compounds of Formula I wherein each of $R_a$ and $R_b$ is hydrogen and $R_1$ is hydroxy are prepared from the corresponding amino acid ester of the structure:

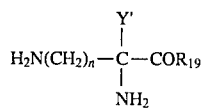

wherein n and Y have the meanings defined in Formula I, and $R_{19}$ is a straight or branched alkoxy group of from 1 to 8 carbon atoms, illustratively methoxy, ethoxy, isopropoxy, butoxy or hexyloxy, by treating said amino acid esters with an appropriate base, such as, sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures of these solvents for from ½ hour to 24 hours at a temperature of from about 0° to 120° C. optionally under a nitrogen atmosphere.

The compounds of Formula III are obtained by procedures generally known in the art from the corresponding amino acid, for example, by treating said amino acid with an appropriate alcohol, for example, methanol, ethanol, isopropyl alcohol, n-butanol or n-heptanol saturated with HCl gas.

The individual optical isomers of the compounds of Formula I wherein each of $R_a$ and $R_b$ is hydrogen and $R_1$ is hydroxy are obtained from the lactam of said compounds using a (+) or (−) binaphthylphosphoric acid salt by the method of R. Viterbo et al, Tetrahedron Letters, 48, 4617 (1971). Other resolving agents such as (+) camphor-10-sulfonic acid may also be employed. The individual optical isomers of compounds of Formula I wherein R is other than hydrogen and $R_1$ is other than hydroxy are obtained as described herein for the racemate only starting with the resolved free amino acid.

The following Examples illustrate the preparation of the compounds of Formula I and the preparation of certain pharmaceutical compositions suitable for oral or injectable administration.

EXAMPLE 1

Dibenzaldimine Ornithine Methyl Ester

L-ornithine hydrochloride, 18 kg and 90 l of methanol are stirred at room temperature to obtain a reasonably uniform suspension. Hydrogen chloride gas is added to this suspension first passing into solution and then precipitating as the ester dihydrochloride. The introduction of hydrogen chloride is stopped and the reaction mixture is refluxed for one hour. Upon cooling to 5° C. for 3 hours, the ornithine methyl ester dihydrochloride is collected by filtration, washed with cold methanol, and vacuum dried at room temperature, yielding approximately 21.4 kg of material.

Approximately 6.8 kg of ornithine methyl ester dihydrochloride is suspended in 10 l of methylene chloride, cooled to 0° C. and 6.5 kg of benzaldehyde, dissolved in 10 l of methylene chloride, is added at such a rate as to maintain the reaction temperature at 0° to −5° C. The reaction mixture is allowed to warm to room temperature, stirring continued for an additional 2 hours, and 20 l of diethyl ether added thereto. Upon standing overnight, the triethylammonium hydrochloride that precipitates is removed by filtration, and the precipitate is washed with an additional 6.8 liters of diethyl ether. The combined filtrates are evaporated in vacuo and the residue dissolved in 34 l of diethyl ether. The organic solution is washed four times with 4 l of water, dried over anhydrous sodium sulfate, filtered and evaporated in vacuo to yields 9.28 kg of dibenzaldimine ornithine methyl ester as an oil.

EXAMPLE 2

2,5-Diamino-2-difluoromethylpentanoic acid (α-DFMO)

Tetrahydrofuran, 15 liters, are cooled to a temperature of −80° C. by the introduction of liquid nitrogen. Di-isopropylamine, 2.82 liters, is added under an atmosphere of nitrogen and twelve liters of a 15% solution of n-butyl-lithium, which is dissolved in hexane, is added to this mixture at such a rate as to maintain the temperature of the mixture at −75° to −80° C. To this mixture, still under nitrogen, is added 5.12 kg of dibenzaldimine ornithine methyl ester dissolved in 15 liters of tetrahydrofuran at such a rate that the reaction temperature remains between −75° and −80° C. The temperature of the reaction mixture is gradually increased to approximately 35° or 40° C. and maintained at that temperature under nitrogen for one hour. The nitrogen gas is replaced and approximately 13 kg of chlorodifluoromethane gas (Freon® 22) is added at such a rate as to maintain the reaction mixture at a temperature of 40° to 50° C. To this mixture is added 20 l of an aqueous saturated sodium chloride and 75 l of diisopropyl ether. The organic layer is separated and the aqueous layer extracted with 25 l of diisopropyl ether. The organic extracts are combined, washed four times with 20 l of aqueous saturated sodium chloride, dried over anhydrous sodium sulfate, filtered, and the filtrate evaporated in vacuo to an oil.

The oil residue is hydrolyzed with 30 l of 1N-hydrochloric acid at room temperature for 3 hours, and reaction mixture is extracted three times with 5 l of chloroform. The combined aqueous layers are stirred for 15 hours at room temperature with 30 l of 10N hydrochloric acid. The reaction mixture is extracted three times with 5 l of chloroform and the aqueous layer separated and evaporated in vacuo, diluted with 8 l of water and evaporated again in vacuo to remove the major portion of the acid present. The residue is diluted with 6 l of water and triethylamine added to a pH of 3.3. Charcoal, 100 g, is added to the mixture and the mixture warmed to 60°–70° C. for two hours. The mixture is filtered, washed with two liters of water and 80 l of acetone added to the filtrate. Upon standing overnight, the crude α-difluoromethylornithine which is obtained (2.1 kg) is filtered and washed with 2 liters of ethanol. Two recrystallizations of a portion of this crude material from a water-ethanol mixture yields 2,5-diamino-2-difluoromethylpentanoic acid, m.p. 183° C.

EXAMPLE 3

3-amino-3-difluoromethyl-2-piperidone

To a solution of methyl-2-difluoromethyl-2,5-diaminopentanoate-dihydrochloride (2.7 g) in dry methanol (30 ml) is added under nitrogen 2 equivalents of sodium methylate in methanol (0.46 g of sodium in 20 ml of methanol). The reaction mixture is stirred for 3 hours at room temperature then the solvent is evaporated under reduced pressure. The residue is extracted with ether to yield crude 3-amino-3-difluoromethyl-2-piperidone which is purified either by crystallization from CHCl₃/pentane: (mp: 149° C.) or by distillation (bp: 135° C./0.05 mmHg).

EXAMPLE 4

(−) and (+) 2-Amino-3-difluoromethyl-2-piperidone hydrochloride

To a solution of (−) binaphthylphosphoric acid (BNPA) (1.27 g) in hot ethanol (50 ml) is added a solution of (±) 3-amino-3-difluoromethyl-2-piperidone (0.546 mg) in hot ethanol (5 ml). On cooling, crystals separate, The reaction mixture is then let stand at 4° C. overnight. The precipitate is filtered off, washed with ethanol and diethyl ether to give 0.54 g of (−) binaphthylphosphoric salt ([α]$_D$=−409° C.=0.3, MeOH mp: 300° C.). Recrystallization of the mother liquor yields 0.15 g of (−) binaphthylphosphoric salt. Concentration of the filtrate gives 1.1 g of a sticky material which is treated with HCl 3M at room temperature for 3 hours. The (−) BNPA is filtered off and the filtrate concentrated under reduced pressure. Recrystallization of the residue (320 mg) in ethanol affords (+) 3-amino-3-difluoromethyl-2-piperidonemonohydrochloride (160 mg) ([α]$_D$=+18°6, C=1, MeOH mp 238° C.). Treated in the same condition the (−) BNPA salt (436 mg) gives (−) 3-amino-3-difluoromethyl-2-piperidone monohydrochloride (137 mg) which is recrystallized in ethanol (67 mg) ([α]$_D$=−19°, C=1.02 MeOH; mp=240° C. dec.).

(−) and (+) 2-difluoromethyl-2,5-diamino pentanoic acid monohydrochloride (−) 3-Difluoromethyl-3-amino-2-piperidone hydrochloride (60 mg) is heated in HCl 6M (4M) at reflux for 12 hours. After concentration under reduced pressure, the residue is dissolved in water and the pH of the solution is adjusted to 4.5 with a solution of NEt₃. The solution is then concentrated under reduced pressure and the residue extracted many times with chloroform and then recrystallized from H₂O/EtOH to give (+) 2-difluoromethyl-2,5-diamino pentanoic acid monohydrochloride (54 mg) ([α]$_D$=+6°, C=0.48; MeOH; mp≧240° C.) By an identical treatment, (+) 3-difluoromethyl-3-amino-2 -piperidone hydrochloride (96 mg) gives (−) 2-difluoromethyl-2,5-diaminopentanoic acid monohydrochloride (56 mg) ([α]$_D$=−10°, C=0.7 MeOH, mp≧244°).

EXAMPLE 5

2,5-Diamino-2-difluoromethylpentanoic acid

Under nitrogen a solution (500 ml) of 2M butyllithium in hexane is added to a stirred solution of 143.1 ml of diisopropylamine in 1.5 liters of tetrahydrofuran at −78° C. after which 261 g (0.81 mole) of ornithine dibenzylaldimine methyl ester in 1.5 l of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1N HCl (1.5 l) for 3 hours, the mixture extracted several times with chloroform and the aqueous solution evaporated to dryness. The oily residue is refluxed with 12N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7–8 l of acetone. The precipitated product is filtered off and washed with ethanol. The crude product is recrystallized by dissolving in about 150 ml hot water and treatment of the solution with hot ethanol (450 ml). On cooling crystals of 2,5-diamino-2-difluoromethylpentanoic acid hydrochloride monohydrate separate; 71 g (37%), m.p. 183° C.

EXAMPLE 6

2- Amino-5-benzyloxycarbonylamino-2-difluoromethylpentanoic acid

To a solution of the copper salt of 2-difluoromethyl-2,5-diaminopentanoic acid in water, prepared by reacting 2-difluoromethyl-2,5-diaminopentanoic acid monohydrate hydrochloride (2.4 g) with copper carbonate (6 g), is added slowly at 0° C. with stirring 1.1 g of benzylchloroformate. The reaction mixture is stirred for an additional 3 hours at room temperature after which hydrogen sulfide is passed through the solution until it becomes colorless. The precipitate is filtered off, and the pH of the aqueous solution is adjusted to 6 by the addition of hydrochloric acid. Upon concentration 2-amino-5-benzyloxycarbonylamino-2-difluoromethylpentanoic acid is obtained.

By the above procedure only using tert-butoxycarbonylazide, acetylchloride or benzoylchloride in place of benzylchloroformate gives respectively 2-amino-5-tert-butoxycarbonylamino-2-difluoromethylpentanoic acid, 5-acetylamino-2-amino-2-difluoromethylpentanoic acid and 2-amino-5-benzyloxycarbonyl-2-difluoromethylpentanoic acid.

EXAMPLE 7

2-Acetylamino-5-amino-2-difluoromethylpentanoic acid

To a solution of 2.9 g of 2-amino-5-tert-butoxycarbonylamino-2-difluoromethylpentanoic acid in 10.5 ml of 1M sodium hydroxide is added at 0° C. simultaneously 0.19 g of acetylchloride and 5 ml of 2M aqueous sodium hydroxide. The reaction mixture is stirred for 3 hours at room temperature. The alkaline aqueous solution is then adjusted to a pH of 2 with hydrochloric acid and extracted with ethylacetate. After usual work-up the solvent is evaporated and the residue taken up in trifluoroacetic acid. After concentration and purification by ion exchange chromatography on a resin 5-amino-2-acetylamino-2-difluoromethylpentanoic acid is obtained.

EXAMPLE 8

5-Amino-2-difluoromethyl-2-(2-aminopropionlylamino)pentanoic acid

To a solution of 3.2 g of 2-amino-5-benzyloxycarbonylamino-2-difluoromethylpentanoic acid in 10 ml of 1M aqueous sodium hydroxide is added at 0° C. simultaneously a solution of tert-butoxycarbonylazide, prepared from 3 g of tert-butoxycarbonylhydrazine, and a solution of 5.5 ml of 2M aqueous sodium hydroxide. The reaction mixture is stirred overnight then extracted twice with 50 ml of ether. The alkaline aqueous solution is then adjusted to a pH of 2 with hydrochloric acid and extracted with ethylacetate. Usual work-up gives a solid residue which is dissolved in 15 ml of dry dimethylformamide and treated at room temperature with 1.6 g of benzylbromide in the presence of 2 ml of dicyclohexylamine. The reaction mixture is stirred for 14 hours and then the precipitate is filtered off. The filtrate is evaporated under reduced pressure. The resulting residue is partitioned between 100 ml of ethylacetate and water. The organic phase is washed successively with 20 ml of 1 normal aqueous hydrochloric acid, 20 ml of water, 20 ml of 5% aqueous sodium bicarbonate, 20 ml of water and 50 ml of brine then dried over magnesium sulfate. The solvent is evaporated and the residue taken up in 10 ml of trifluoroacetic acid. After 1 hour at room temperature the excess trifluoroacetic acid is stripped off under reduced pressure and the residue is taken up in a saturated solution of sodium bicarbonate and extracted with 50 ml of ether. The ether phase is dried over magnesium sulfate and then added at 0° C. to a solution of N-benzyloxycarbonyl-O-ethoxycarbonylalanine (2 g) in 20 ml of ether. Stirring is continued overnight at room temperature. The solvent is evaporated and the resulting syrupy residue is taken up in glacial acetic acid (20 ml) and hydrogenated over Pd/C 10% (200 mg). After completion of the hydrogen uptake the catalyst is filtered off. The filtrate is concentrated under reduced pressure with toluene and the residue purified by ion exchange chromatography on an acidic resin to give 5-amino-2-(2-aminopropionylamino)-2-difluoromethylpentanoic acid.

EXAMPLE 9

2-[(2,5-Diamino-2-difluoromethyl-1-oxopentane)amino]propionic acid

To a solution of 2,5-diamino-2-difluozomethylpentanoic acid monohydrate hydrochloride (2.35 g) in 10 ml of 2M aqueous sodium hydroxide is added at 0° C. simultaneously a solution of 10 ml of 2 molar aqueous sodium hydroxide and a solution of tert-butoxycarbonylazide prepared from 3 g of tert-butoxycarbonylhydrazine. The reaction mixture is stirred overnight at room temperature and then extracted twice with 250 ml portions of ether. The alkaline aqueous solution is adjusted to a pH of 2 with hydrochloric acid and extracted with ethylacetate. After usual work-up the solvent is evaporated and the residue taken up in 40 ml of dry ether. After addition of 1 g of triethylamine an ether solution of 1 g of ethylchloroformate is added slowly at 0° C. with stirring. The precipitate is filtered off and the ether solution is added at once to a solution of alanine tert-butylester (1.5 g). Stirring is continued overnight and the solvent is evaporated. The residue is taken up in trifluoroacetic acid. After concentration and purification by ion exchange chromatography on an Amberlite 1R 120 resin 2-[(2,5-diamino-2-difluoromethyl-1-oxopentane)amino]-propionic acid is obtained.

EXAMPLE 10

2-Fluoromethyl-2,5-diaminopentanoic acid (α-MFMO)

A. 2-Fluoromethyl-2-amino-5-methoxy-valeronitrile

Under an atmosphere of nitrogen, 3-methoxypropyl magnesium chloride is prepared from 3-methoxy-1-chloropropane (5.43 g, 50 mmol, prepared according to Haworth and Perkin, Chem. Zentralblatt II 1271 (1912) and magnesium turnings (1.22 g, 50 mmol) in dry THF (50 ml). The mixture is heated under reflux for 3 hours, then cooled to −30° C. and a solution of fluoroacetonitrile (2.95 g, 50 mmol) in THF (30 ml) is added during 20 minutes. After keeping the mixture at −30° C. for ½ hour more, a solution of sodium cyanide (4.9 g, 100 mmol) and ammonium chloride (8.09 g, 150 mmol) in water (100 mL), previously cooled to 0° C., is added and the mixture is stirred for ¾ hours at room temperature. After saturating with sodium chloride, the THF layer is separated and the aqueous phase is extracted twice with ether. After drying ($Na_2SO_4$), the combined organic extracts are evaporated to give 2-fluoromethyl-2-amino-5-methoxyvaleronitrile (4.0 g) as a brown oil.

NMR ($CDCl_3$) δ: 1.77 (4H, m), 2.10 (broad s, $NH_2$), 3.30 (3H, s), 3.40 (2H, t), 4.32 (2H, ABX, $J_{AB}$=9 Hz, $J_{AX}$=$J_{BX}$=$J_{H-F}$=47 Hz).

B.
2-Fluoromethyl-2-phtalimide-5-methoxy-valeronitrile

To a solution of 2-fluoromethyl-2-amino-5-methoxy-valeronitrile (1.62 g, 10 mmol) and triethylamine (2.02 g, 20 mmol) in methylene chloride (30 mL), cooled to −20° C. is added phthaloyldichloride (2.03 g, 10 mmol) in methylene chloride (10 mL). The mixture is allowed to warm up to room temperature overnight. After washing with water, 1N HCl, water again, and drying ($Na_2SO_4$), the solvent is removed under reduced pressure to give 2.4 g (83%) of crude material. This is purified by chromatography on silica (ethyl acetate/petroleum ether 3:7). NMR ($CDCl_3$): δ2.15 (4H, m), 3.23 (3H, s), 3.40 (2H, t, J=6 Hz), 5.02 (2H, ABX, $J_{AB}$=9 Hz, $J_{AX}$=$J_{BX}$=$J_{H-F}$=46 Hz), 7.77 (4H, s).

C.
2-Fluoromethyl-2-phthalimido-5-iodo-valeronitrile

2-Fluoromethyl-2-phthalimido-5-methoxy-valeronitrile (1.20 g, 4.14 mmol), trimethylsilyl iodide (3.2 g, 16 mmol) and chloroform (15 mL) are heated to 60° C. under nitrogen for 48 hours. After removal of the solvent, the residue is dissolved in chloroform, washed with water, sodium thiosulfate solution and water again, dried and evaporated to give the crude product as an oil (1.2 g). This is purified by chromatography on silica (ethyl acetate/petroleum ether 1:3) to give pure 2-fluoromethyl-2-phthalimido-5-iodo-valeronitrile. NMR ($CDCl_3$) δ: 2.0 (4H, m), 3.10 (2H, t), 4.90 (2H, ABX, $J_{AB}$=9 Hz, $J_{AX}$=$J_{BX}$=$J_{H-F}$=46 Hz), 7.70 (4H, s).

D. 2-Fluoromethyl-2,5-diphthalimido-valeronitrile

2-Fluoromethyl-2-phthalimido-5-iodo-valeronitrile (1.20 g, 3.11 mmol) and potassium phthalimide (0.75 g, 4 mmol) are heated in dimethylformamide (25 mL) to 80° C. for 2 hours. After standing overnight at room temperature, the DMF is removed by vacuum distillation and the residue is dissolved in chloroform and washed with 1N KOH and water. After drying ($Na_2SO_4$), evaporation gives 2-fluoromethyl-2,5-diphthalimido-valeronitrile as a solid.

NMR ($CDCl_3$) δ: 2.17 (4H, m), 3.73 (2H, t), 4.93 (2H, ABX, $J_{AB}$=9 Hz, $J_{AX}$=$J_{BX}$=$J_{H-F}$=46 Hz), 7.73 (8H, broadened s).

E. 2,5-Diamino-2-fluoromethyl pentanoic acid

2-Fluoromethyl-2,5-diphthalimido valeronitrile (1.21 g, 3 mol) is refluxed with conc. hydrochloric acid (20 mL) for 4 days. After standing at room temperature for several hours, phthalic acid is removed by filtration, the filtrate is evaporated, the residue dissolved in 2N HCl (20 mL) and carefully extracted with ether (5×10 mL). After evaporation, the residue is dried carefully under vacuum (oil pump) overnight. It is dissolved in dry ethanol (7 mL) and, after filtration, propylene oxide (0.3 g, 5 mmol) in ethanol (1 mL) is added to precipitate the monohydrochloride. This is collected after standing overnight at room temperature and recrystallized from water/ethanol to give pure 2,5-diamino-2-fluoromethylpentanoic acid, monohydrochloride; m.p. 260° C. (dec), TLC (EtOH/$NH_4OH$ 80/20): 0.18.

NMR ($D_2O$) δ: 1.93 (4H, m), 3.10 (2H, broad t), 4.83 (2H, ABX, $J_{AB}$=10 Hz, $J_{AX}$=$J_{BX}$=$J_{H-F}$=46 Hz).

EXAMPLE 11

An illustrative composition for hard gelatin capsules is as follows:

| (a) 2,5-diamino-2-difluoromethyl pentanoic acid | 200 mg |
|---|---|
| (b) talc | 5 mg |
| (c) lactose | 10 mg |

The formulation is prepared by passing the dry powders of (a) and (b) through a fine mesh screen and mixing them well. The powder is then filled into hard gelatin capsules at a net fill of 215 mg per capsules.

EXAMPLE 12

An illustrative composition for tablets is as follows:

| (a) 2,5-diamino-2-difluoromethylpentanoic acid | 200 mg |
|---|---|
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 290 mg each.

EXAMPLE 13

An illustrative composition for an injectable suspension is the following 1 ml ampul for an intramuscular injection.

| | Weight percent |
|---|---|
| (a) 2,5-diamino-2-difluoromethylpentanoic acid | 20 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 200 mg per ml of novel compound (a).

What is claimed is:

1. A method of controlling tumor growth susceptible to treatment with the combination below in a patient in need thereof comprising concomitantly administering to said patient an effective anti-tumor amount of methylglyoxal bis(guanylhydrazone) and an effective polyamine biosynthesis inhibitory amount of α-difluoromethyl ornithine or a pharmaceutically acceptable salt thereof.

2. A process of claim 1 wherein the tumor to be treated is lymphoma.

3. A process of claim 1 wherein the tumor to be treated is Hodgkins Disease.

* * * * *

UNITED STATES PATENT AND TRADEMARK OFFICE
CERTIFICATE OF CORRECTION

PATENT NO. : 5,614,557
DATED : March 25, 1997
INVENTOR(S) : Philippe Bey and Michel Jung It is certified that error appears in the above-identified patent and that said Letters Patent is hereby corrected as shown below:

Column 2, Line 44 of Patent reads "intented" and should read --intended--.

Column 8, Line 18 of Patent reads "on with" and should read --or with--.

Column 8, Line 59 of Patent reads "etherst" and should read --ethers--.

Column 8, Line 66 of Patent reads "trimethyloxonlure" and should read --trimethyloxonium--.

Column 11, Line 45 of Patent reads "wherein in $R_1$" and should read --wherein $R_1$.

Column 11, Line 59 of Patent reads "abut" and should read --about--.

Column 14, Line 30 Patent reads "(4M) and should read --(4 ml)--.

Column 15, Line 55 of Patent reads "aminopropionlylamino" and should read --aminopropionylamino--.

Column 16, Line 33 of Patent reads "difluozomethylpentanoic" and should read --difluoromethylpentanoic--.

Signed and Sealed this

Fifteenth Day of September, 1998

Attest:

Attesting Officer

BRUCE LEHMAN

Commissioner of Patents and Trademarks